(12) United States Patent
Miller et al.

(10) Patent No.: US 6,369,247 B1
(45) Date of Patent: Apr. 9, 2002

(54) PROCESS FOR OXIDATION OF STEROIDAL COMPOUNDS HAVING ALLYLIC GROUPS

(75) Inventors: Ross A. Miller, Fanwood; Andrew S. Thompson, Mountainside; Raman K. Bakshi, Edison; Edward G. Corley, Old Bridge, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 08/718,408

(22) PCT Filed: May 15, 1995

(86) PCT No.: PCT/US95/06004

§ 371 Date: Sep. 30, 1996

§ 102(e) Date: Sep. 30, 1996

(87) PCT Pub. No.: WO95/32215

PCT Pub. Date: Nov. 30, 1995

Related U.S. Application Data

(63) Continuation of application No. 08/245,935, filed on May 19, 1994, now abandoned.

(51) Int. Cl.$^7$ .................................................. C07J 9/00
(52) U.S. Cl. .......................... 552/542; 552/636; 540/2; 540/106
(58) Field of Search ................................. 502/243, 254, 502/261; 540/2, 106; 552/542, 636

(56) References Cited

U.S. PATENT DOCUMENTS 5,030,739 A  7/1991  Foricher et al. ............. 552/542

FOREIGN PATENT DOCUMENTS

| EP | 0 174 194 | 3/1986 |
| WO | WO 93/23419 | 11/1993 |
| WO | WO 95/13077 | 5/1995 |

OTHER PUBLICATIONS

Muzart, "Synthesis of unsaturated carbonyl compounds via a chromium–mediated allylic oxidation by 70% tert.butyl-hydroperoxide". Tet. Letters, vol. 28, pp. 4665–4668, 1987.*
Neumann et al., "Alkene oxidation catalyzed by a ruthenium–substituted heteropolyanion". J. Am. Chem. Soc., vol. 112, pp. 6025–6031, 1990.*
Pearson et al., "A new method for the oxidation of alkenes to enones . . . ". J. Chem. Soc., Perkins Trans. I, 1985.*
Reddy et al., Tet. Letters, vol. 36 (1995), pp. 159–162, "Cobalt catalyzed oxidation of cyclic alkenes with molecular oxygen . . . ".
Kimura et al., Chem. Pharm. Bull. , vol. 28 (1980), pp. 1836–1841, The reactions of cholesteryl acetate with various hydroperoxides in the presence of tris(acetylacetonato)iron (III) . . . .
Sharpless et al., Aldrichimica Acta, vol. 12 (1979), pp. 63–73, Metal–catalyzed, highly selective oxygenations of olefins and acetylenes with tert–butyl hydroperoxide . . . .
Murahashi et al., Tet. Letters, vol. 34 (1993), pp. 1299–1302, "Ruthenium–catalyzed cytochrome P–450 type oxidation of alkanes with alkyl hydroperoxides".
Muzart, Tet. Letters, vol. 28 (1987), pp. 4665–4668, "Synthesis of unsaturated carbonyl compounds via a chromium-mediated allylic oxidation by 70% tert.butylhydroperoxide".
Neumann et al., J. Am. Chem. Soc., vol. 112 (1990), pp. 6025–6031, Alkene oxidation catalyzed by a rutheniumsubstituted heteropolyanion . . . .
Parish et al., Chem. of Physics of Lipids, vol. 36 (1984), pp. 179–188, "Chemical synthesis of 4,4'–dimethyl–7–oxygenated sterols . . . ".
Pearson et al., J. Chem. Soc. (Perkins Trans. I), (1985), pp. 267–273, "A new method for the oxidation of alkenes to enones . . . ".
Kimura et al., Chem. Pharm. Bull, vol. 29 (1981), pp. 35–42, "The reactions of cholesteryl acetate with tert–butyl hydroperoxide and molybdenum complexes".
Neumann et al., J. of Chem. Soc., Chem. Commun., vol. 18 (1989), pp. 1324–1325, "A ruthenium heteropolyanion as catalyst for alkane and alkene oxidation".
Miller et al., Tet. Letters, vol. 37 (1996), pp. 3429–3432, "A ruthenium catalyzed oxidation of steroidal alkenes to enones".
Harre et al., Organic Process Res. & Dev., vol. 2 (1998), pp. 100–104, "Some reaction safety aspects of ruthenium–catalyzed allylic oxidations of delta–5–steroids in the pilot plant".
Reddy et al., Tet. Letters, vol. 36 (1995), pp. 159–162, "Cobalt catalyzed oxidation of cyclic alkenes with molecular oxygen: Allylic oxidation versus double bond attack".

* cited by examiner

Primary Examiner—Barbara P. Badio
(74) Attorney, Agent, or Firm—Catherine D. Fitch; Melvin Winokur

(57) ABSTRACT

The instant invention involves a process for oxidizing compounds containing an allylic group, i.e. those containing an allylic hydrogen or allylic alcohol group, to the corresponding enones, using a ruthenium-based catalyst in the presence of a hydroperoxide. Particularly, Δ-5-steroidal alkenes can be oxidized to the corresponding Δ-5-7-keto alkenes.

25 Claims, No Drawings

PROCESS FOR OXIDATION OF STEROIDAL COMPOUNDS HAVING ALLYLIC GROUPS

CROSS-REFERENCE TO RELATED APPLICATIONS

The present application is a national phase application under 35 U.S.C. §371 of PCT application PCT/US95/06004, filed May 15, 1995, which in turn claims priority to continuation U.S. patent application Ser. No. 08/245,935, filed May 19, 1994, now abandoned.

FIELD OF THE INVENTION

The present invention is concerned with a novel process for the catalytic oxidation of compounds containing an allylic group using ruthenium based catalysts. The process is generally useful for the oxidation of compounds containing allylic hydrogens or alcohols, and particularly for Δ-5 steroidal compounds.

BACKGROUND OF THE INVENTION

The principal mediator of androgenic activity in some target organs, e.g. the prostate, is 5α-dihydrotestosterone ("DHT"), formed locally in the target organ by the action of 5α-reductase, which converts testosterone to DHT. Certain undesirable physiological manifestations, such as acne vulgaris, seborrhea, female hirsutism, androgenic alopecia which includes female and male pattern baldness, and benign prostatic hyperplasia, are the result of hyperandrogenic stimulation caused by an excessive accumulation of testosterone ("T") or similar androgenic hormones in the metabolic system. Inhibitors of 5α-reductase will serve to prevent or lessen symptoms of hyperandrogenic stimulation in these organs. See especially U.S. Pat. No. 4,377,584, issued Mar. 22, 1983, and U.S. Pat. No. 4,760,071, issued Jul. 26, 1988, both assigned to Merck & Co., Inc. It is now known that a second 5α-reductase isozyme exists, which interacts with skin tissues, especially in scalp tissues. See, e.g., G. Harris, et al., Proc. Natl. Acad. Sci. USA, Vol. 89, pp. 10787–10791 (November 1992). The isozyme that principally interacts in skin tissues is conventionally designated as 5α-reductase 1 (or 5α-reductase type 1), while the isozyme that principally interacts within the prostatic tissues is designated as 5α-reductase 2 (or 5α-reductase type 2).

The oxidation of Δ-5-steroidal alkenes to the corresponding enones is an important step in the synthesis of steroid end-products useful as 5α-reductase inhibitors. Chromium based oxidations have previously been used for the oxidation of allylic groups, but are environmentally unacceptable and require silica gel chromatography. The instant invention provides an improved alternative method for oxidizing Δ-5-steroidal alkenes, which is convenient to run, and is environmentally friendly. Furthermore, the yield and purity of the oxidized intermediate obtained by the instant process meets or exceeds those obtained when other previously known oxidation methods are used.

SUMMARY OF THE INVENTION

The novel process of this invention involves the oxidation of compounds containing an allylic alcohol group or allylic hydrogens to the corresponding enones using a ruthenium based catalyst in the presence of a hydroperoxide. Particularly, this invention involves conversion of Δ-5-steroidal alkenes to Δ-5-7-keto-steroidal alkenes, using a ruthenium based catalyst in the presence of a hydroperoxide. This novel process can be exemplified in the following embodiment:

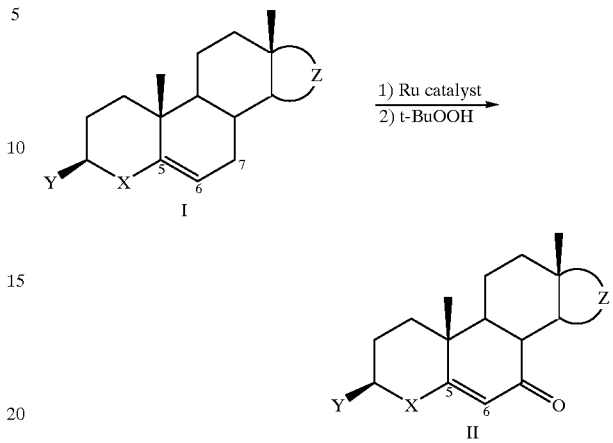

Compounds of Formula II are useful as intermediates in the preparation of 7β-substituted 3-keto-4-azasteroid compounds, such as those which are 5α-reductase inhibitors. 5α-Reductase inhibitors are useful in the treatment of hyperandrogenic disorders such as benign prostatic hyperplasia, acne vulgaris, seborrhea, female hirsutism, androgenic alopecia, male pattern baldness, and the prevention and treatment of prostatic carcinoma.

DETAILED DESCRIPTION OF THE INVENTION

The novel process of this invention involves the discovery that steroidal compounds containing a C5–C6 double bond (i.e., Δ-5-steriodal alkenes) can be oxidized to the corresponding 7-keto compounds by treatment with a hydroperoxide in the presence of a ruthenium-based catalyst. Using the same process, compounds containing an allylic alcohol group can likewise be oxidized to their corresponding ketones. For reference, the standard numbering around the unsubstituted core steroid structure and the letter designation of the rings is as follows:

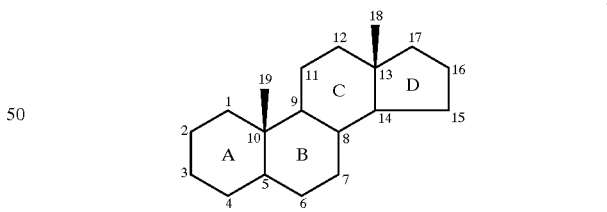

It has surprisingly been discovered that the instant oxidation process will proceed using any catalyst which is ruthenium based. Many ruthenium based catalysts are known in the art, and any such ruthenium based catalyst can be used with the instant process. Examples of ruthenium based catalysts that may be used in this process include but are not limited to the following: $RuW_{11}O_{39}SiNa_5$, $RuCl_3$, $RuCl_2(PPh_3)_3$, $Ru(acac)_3$, $Ru(dimethylglyoximato)_2(PPh_3)_2$, $RuO_2$, $Ru(TPP)(CO)(THF)$, $Ru(bipy)_2Cl_2$, $Ru(TPP)(CO)(THF)$, Ru/C and $K_5SiRu(H_2O)W_{11}O_{39}$. "TPP" is tetraphenylporphine; "acac" is acetylacetonate; "bipy" is bipyridine. Ruthenium based catalysts are described in, e.g., R.

Neuman, *J. Am. Chem. Soc.*, Vol. 112, 6025 (1990); S-I. Murahashi, *Tetrahedron Letters*, Vol. 34, 1299 (1993).

Particularly, a ruthenium sodium tungstate-based catalyst is used, and more particularly $RuW_{11}O_{39}SiNa_5$. A catalytic amount of the ruthenium compound is used in this reaction. Those skilled in the art are familiar with the use of catalytic amounts of reaction catalysts, and will appreciate that the amount of catalyst that can be used may vary with the scale of the reaction and the particular ruthenium based catalyst employed. An exemplary amount of the ruthenium based catalyst ranges from about 0.05 to 5 mol %, and particularly about 0.5 mol % of catalyst per mole % of starting material, but variations beyond this range would be acceptable as well.

The alkene starting material is treated with a hydroperoxide in the presence of the ruthenium-based catalyst for conversion to the corresponding enone. Many hydroperoxides are known in the art, and any such hydroperoxide can be used with the instant process. Examples of hydroperoxides that may be used in this process include but are not limited to t-butyl hydrogen peroxide (t-BuOOH), cumene hydroperoxide, hydrogen peroxide, and benzoyl peroxide, with t-BuOOH being preferred. An amount of hydroperoxide sufficient to complete the oxidation should be used, for example at least about 2 moles, and preferably about 8 to 10 moles per mole of starting material.

Any commercially available solvent or combinations thereof may be employed in the instant process step, such as alkanes, ethers, alcohols, halogenated solvents, water, etc. Examples of the variety of solvents that may be used include but are not limited to toluene, ethyl acetate, hexane, chlorobenzene, heptane, t-butyl methyl ether (MTBE), benzene, acetonitrile, cyclohexane, methylene chloride, 1,2-dichloroethane and t-butyl alcohol (t-BuOH), or a combination thereof. When using $RuW_{11}O_{39}SiNa_5$ as the catalyst, heptane is the preferred solvent. With $RuCl_2(PPh_3)_3$, chlorobenzene or benzene are preferred solvents.

This oxidation process may be run at a temperature between about −20° C. and up to the reflux temperature of the solvent used, for example about 100° C., and particularly between about 5° C. and 50° C., and more particularly at about 15° C. The reaction may be run at any pH, and particularly at an acidic pH, and more particularly at a pH of about 1. The pH of the reaction mixture may be adjusted prior to addition of t-BuOOH by addition of an aqueous acid such as sulfuric acid. Although not required, the reaction is preferably run under an inert atmosphere, such as nitrogen or argon.

Δ-5-Steroidal alkenes that can be used in this process are known in the art. For example, see those listed and available through the Sigma Chemical Co.

One embodiment of the present invention comprises the step of treating a compound of Formula I

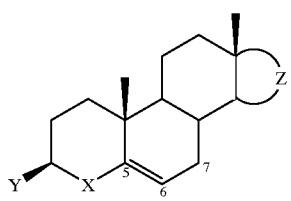

I with a hydroperoxide in the presence of a ruthenium based catalyst in a solvent to form a compound of Formula II

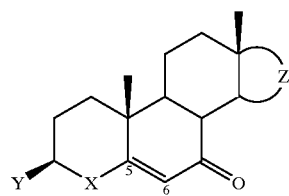

II wherein Y is hydroxy, an esterified hydroxy group, keto or ethylene ketal, X is —$CH_2$—, —NH—, or —N($CH_3$)— or —N-2,4-dimethoxybenzyl, and Z is

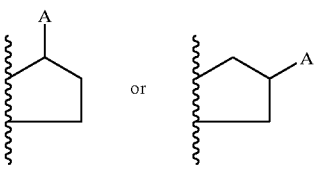

The oxidation reaction is not affected by the substituent at the 16- or 17-position of the steroid, and thus "A" can be any synthetically feasible substituent. The flexibility and broad applicability of the instant process is demonstrated by the fact that it is not limited by the choice of substituent at the 16- and 17-positions of the steroidal starting material.

Representative examples of "A" include but are not limited to: —H; keto (=O); protected hydroxy, e.g. dimethyl-t-butyl silyloxy, trimethylsilyloxy, tri-ethylsilyloxy, tri-i-propylsilyloxy, triphenylsilyloxy; acetate; hydroxy; protected amino, e.g. acetylamino; amino; $C_{1-10}$ alkyl, e.g. methyl, ethyl, 1,5-dimethylhexyl, 6-methylhept-2-yl cholestanyl 17-side chain, pregnane or stigmasterol 17-side chain; aryl substituted $C_{1-10}$ alkyl, e.g. omega-phenylpropyl, 1-(chlorophenoxy)ethyl; aryl carbamoyl substituted $C_{1-10}$ alkyl, e.g. 2-(4-pyridinyl-carbamoyl) ethyl; $C_{1-10}$alkylcarbonyl, e.g. isobutylcarbonyl; arylcarbonyl, e.g. phenylcarbonyl; ether-substituted $C_{1-10}$alkyl, e.g. 1-methoxy-ethyl, 1-ethoxy-ethyl; keto-substituted $C_{1-10}$alkyl, e.g. 1-keto-ethyl; heteroaryl-substituted $C_{1-10}$ alkyl, e.g. omega-(4-pyridyl)-butyl; carboxy; carboxylic esters, e.g. $C_{1-10}$ alkylcarboxylic esters such as carbomethoxy; carboxamides, e.g. $C_{1-10}$ alkylcarboxamides or aralkylcarboxamides such as N,N-diisopropyl carboxamide, n-t-butyl carboxamide or N-(diphenylmethyl)-carboxamide; carbamates such as $C_{1-10}$ alkylcarbamates, especially t-butylcarbamate; substituted or unsubstituted anilide derivatives wherein the phenyl may be substituted with 1 to 2 substitutents selected from ethyl, methyl, trifluoromethyl or halo (F, Cl, Br, I); ureas, e.g. $C_{1-10}$ alkylcarbonylamino ureas such as t-butylcarbonylamino urea; $C_{1-10}$ alkylcarbonylamino, e.g. t-butylcarbonylamino; ethers, e.g. n-butyloxy, ethylene ketal; substituted and unsubstituted aryl ethers such as chlorophenyloxy, methylphenyloxy, phenyloxy, methylsulfonylphenyloxy, pyrimidinyloxy; and the like.

The term "alkyl" includes both straight and branched chain alkyl groups, and "aryl" includes phenyl, pyridinyl and pyrimidinyl.

Hydroxy and amino protecting groups are known to those of ordinary skill in the art, and any such groups may be used. For example, acetate, benzoate, ether and silyl protecting groups are suitable hydroxy protecting groups. Standard silyl protecting groups have the general formula —$Si(Xa)_3$, wherein each Xa group is independently an alkyl or aryl group, and include, e.g. trimethylsilyl, tri-ethylsilyl, tri-i-propylsilyl, triphenylsilyl as well as t-butyl-di-(Xb)-silyl where Xb is methyl, ethyl, i-propyl or phenyl (Ph). Standard amino protecting groups have the general formula —C(O)-Xc, wherein Xc is alkyl, aryl, O-alkyl or O-aryl, and include, e.g. N-t-butoxycarbonyl. See also *Protective Groups in Organic Synthesis,* T. W. Green et al. (John Wiley and Sons, 1991) for descriptions of protecting groups.

As will be appreciated by those of ordinary skill in the art, when Y is an esterified hydroxy group, substituents such as those of Formula III are intended

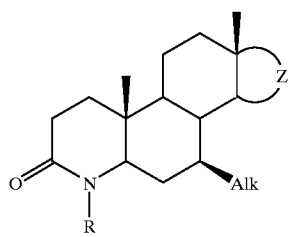

III wherein Xd can form any synthetically feasible ester group. The process is not limited by the choice of any particular ester form for Y. Representative examples of Xa include but are not limited to straight or branched chain alkyl, e.g. $C_{1-18}$ alkyl, phenyl, mono- or di-substituted phenyl wherein the substituents include, e.g., halogen, alkoxy, and amino.

The intermediate compound II is useful for making 7β-substituted 4-azasteroid compounds, and particularly those which are inhibitors of 5α-reductase. Examples of such compounds include but are not limited to those disclosed in U.S. Pat. Nos. 4,377,584 and 4,760,071; WO 93/23419; and WO 93/23420. More particularly, compounds that can be made from intermediate II include those of general Formula IV:

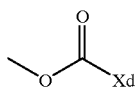

IV wherein R is H or methyl, Z is

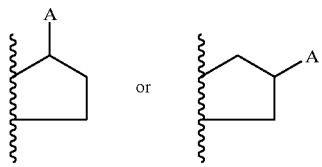

and Alk is selected from $C_{1-25}$ linear or branched alkyl, e.g., methyl (Me), ethyl (Et), propyl (Pr), isopropyl (i-Pr), n-butyl (n-Bu), sec-butyl, isobutyl, tert-butyl (t-Bu) and the like; $C_{3-6}$ cycloalkyl, e.g., cyclopropyl, cyclobutyl, cyclopentyl and cyclohexyl; and allyl. Processes for making such compounds are taught for example in U.S. Pat. No. 5,237,064, WO 93/23419 and WO 93/23420 and PCT application having the Ser. No. 94/12071.

A further exemplary synthetic scheme showing how to make compounds of Formula IV is as follows:

REACTION SCHEME

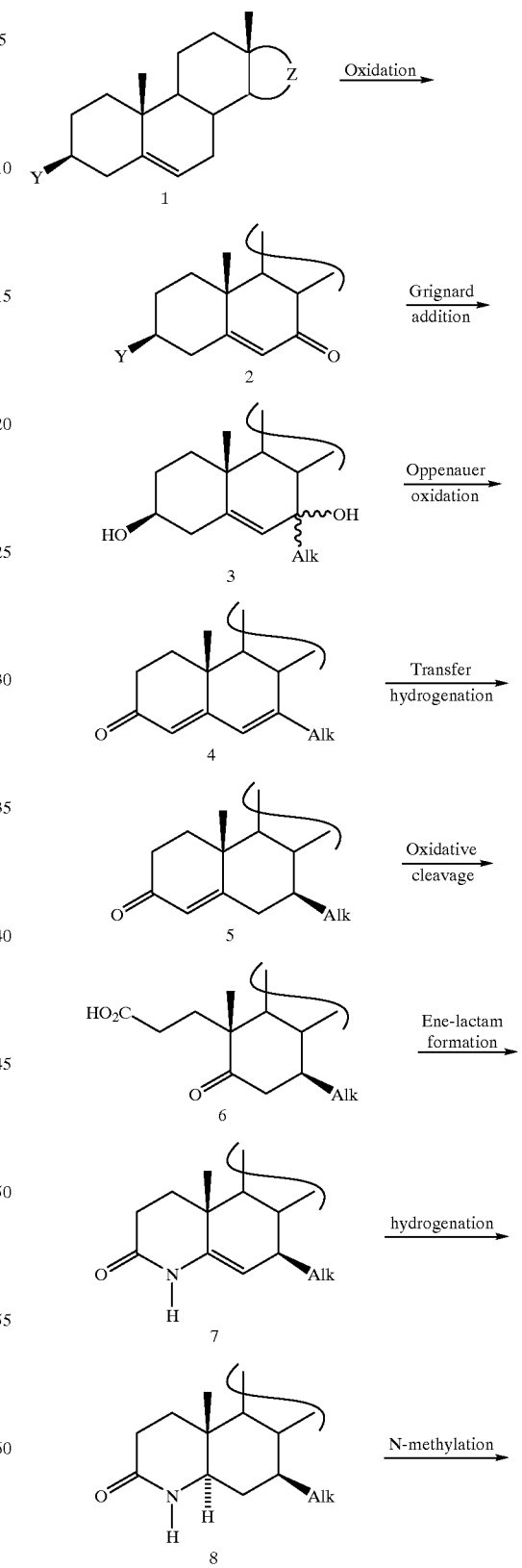

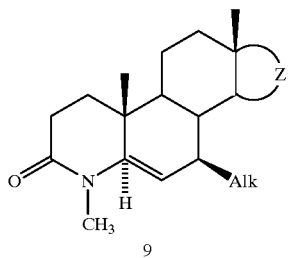

The starting materials for the process generally are the 3-acetoxy-androst-5-enes which are known and available in the art.

Z is

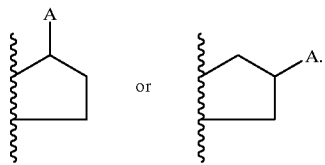

The term "A" is described above and can be any substituent preferably inert and non-interfering under the particular reaction conditions of each step outlined in the above reaction scheme.

The A group can also be a protected hydroxy or protected amino group which undergoes the indicated reaction sequence and then is subsequently removed, or it can also be removed during a particular step providing it does not interfere with the indicated reaction. For example, where A is —O-TBDMS, i.e., t-butyldimethylsilyloxy, the silyl protecting group can be removed during e.g., the ring closure step of the seco acid 6 to the 4-aza steroid 7, such that the subsequent steps are performed on the 16- or 17-OH compound. Also, the starting A group can be a precursor to the finally desired A group and be converted thereto concurrently in one of the steps. For example, where A contains a double bond, e.g., a stigmasterol analog, the double bond in the 16- or 17-side chain may also be oxidized during the seco acid formation in going from 5 to 6.

As shown in the above Reaction Scheme, the "Alk" substituent can be introduced onto the B ring of the 4-aza steroid generally by the application of an organometallic carbonyl addition reaction, e.g., the Grignard reaction in which the 7-carbonyl group can be reacted with the Grignard reagent containing "Alk" as the R radical in RMgX. The Grignard reaction conditions are conventional and include the use of, e.g., methyl, allyl or cycloalkyl magnesium chloride, ethyl magnesium bromide, cyclopropyl magnesium bromide, and the like. Preferably, the Grignard reagent is used with $CeCl_3$. Usable dry solvents include, e.g., tetrahydrofuran (THF), diethyl ether, dimethoxyethane, and di-n-butyl ether. The reaction is conducted under dry conditions generally in the temperature range of 0° C. to 40° C. Generally, the reaction requires about 6 to 24 hours for completion. Other organometallic carbonyl addition reactions can be used in this step, such as those utilizing lithium and zinc organometallic reagents which are known in the art.

The adduct 3 is then oxidized with e.g. aluminum isopropoxide and cyclohexanone (Oppenauer oxidation conditions) in e.g. refluxing toluene solvent to produce the 7-alkyl-4,6-dien-3-one 4. Other reagents which can be used are, e.g., aluminum ethoxide or aluminum t-butoxide. Other solvents which can be used include, e.g., methylethylketone (MEK) and xylene. The temperature is generally in the range of about 60 to 120° C., and the reaction is carried out under anhydrous conditions and generally requires about 2 to 24 hours for completion.

The dien-3-one 4 is next converted to the 4-ene 5 by treatment with Pd on carbon, DBU, and cyclohexene in a solvent such as ethanol.

The A Ring is next cleaved by treatment with e.g. potassium permanganate, sodium periodate in e.g., t-butylalcohol at 80° C. to produce the corresponding seco-acid 6. Other oxidation reagents which can be used include ruthenium tetraoxide and ozone. Other solvents which can be used are: $CH_3CN$, $CCl_4$, methanol (MeOH) and $CH_2Cl_2$. The reaction generally requires about 2 to 4 hours to proceed to completion.

The seco-acid in a $C_{2-4}$ alkanoic acid such as acetic acid (HOAc) is treated with ammonium acetate at about 15–30° C. followed by warming to reflux for about 2 to 4 hours. After cooling to about 50–70° C., water is added and the mixture seeded to cause crystallization of the ene-lactam 7.

Hydrogenation of the ene-lactam is accomplished with a noble metal catalyst, such as a $Pd(OH)_2$, $PtO_2$, Pd on carbon, Rh on carbon or $Rh/Al_2O_3$, and preferably using Rh on carbon or $Rh/Al_2O_3$, in a $C_{2-4}$ alkanoic acid, such as acetic acid, or an alcohol such as ethanol, or ethyl acetate, at about 50–70 psi hydrogen. The reaction is run at about 15–25° C. for about 8 to 12 hours, and then the temperature may be raised, e.g., to about 50–70° C., until the reaction is essentially complete. The catalyst is removed by filtration and the filtrate is concentrated to dryness. The product 8 may then be purified, e.g., by recrystallization.

The last step, N-methylation, is accomplished by treating a solution of the lactam 8 in an aromatic solvent such as benzene or toluene, in the presence of tetrabutylammonium hydrogensulfate and aqueous alkali such as potassium hydroxide or sodium hydroxide, with methyl chloride gas with rapid stirring at about 40–60° C. until the reaction is essentially complete, usually in about 20–30 hours.

Representative experimental procedures utilizing the novel process are detailed below. These procedures are exemplary only and should not be construed as being limitations on the novel process of this invention.

EXAMPLE 1

Preparation of 4,7β-dimehyl-4-aza-5α-cholestan-3-one

Step 1:

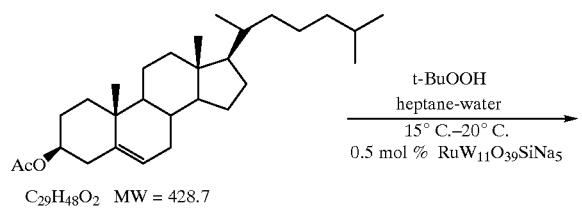

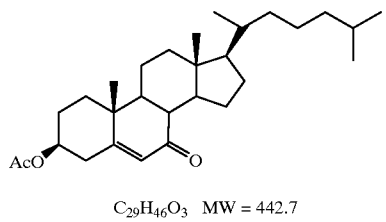

$C_{29}H_{46}O_3$  MW = 442.7

| Materials | Amt | | Mole | MW |
|---|---|---|---|---|
| Cholesteryl acetate (95% Aldrich) | 78.1 | gm | 0.173 | 428.7 |
| t-BuOOH (70 wt %, Aldrich) | 189 | gm | 1.46 | 90.12 |
| $Na_2WO_4$-$2H_2O$ | 3.3 | gm | 0.010 | 329.9 |
| $RUCl_3$-$xH_2O$ | 0.24 | gm | 0.00116 | 207.43 |
| Sodium metasilicate ($Na_2SiO_3$) | 0.315 | gm | 0.00258 | 122.06 |
| Sulfuric acid (d = 1.84 g/mL, 18 M) | 0.45 | mL | 0.0081 | 98.08 |
| Sodium sulfite ($Na_2SO_3$) | 39 | gm | 0.309 | 126.04 |
| heptane | 300 | mL | | |
| MBK (methyl ethyl ketone) | 550 | mL | | |
| water | 460 | mL | | |

In a 2000 mL 3-necked flask was added sodium tungstate dihydrate (3.3 gm), sodium metasilicate (0.315 gm) and 70 mL water and stirred until homogeneous. The solution was neutralized (pH=6–7) with concentrated sulfuric acid (0.45 mL). A 4° C. exotherm was noted for the addition of acid. Ruthenium trichloride hydrate (240 mg) was added and the mixture stirred for 10 min. Cholesteryl acetate (78.1 gm) and heptane (300 mL) were added to the catalyst mixture. The stirring rate was 225–275 rpm with an overhead paddle stirrer.

70% t-BuOOH (189 gm) was added over 5–10 min. An internal temperature of 15–20° C. was maintained by cooling with a water bath. The temperature of the batch began to rise slowly after an induction period of 5–15 min. The reaction was stirred until less than 1.5 wt % of s.m. (starting material) and less than 2% of the 7-hydroxy cholesteryl acetate intermediate remained, about 20–24 hrs.

The reaction was monitored with a YMC basic column, 90:10 acetonitrile:water, flow rate=1.5 mL/min, UV detection at 200 nm. Retention times: $t_R$ cholesteryl acetate=17.0 min, $t_R$ 7-keto cholesteryl acetate=7.8 min, $t_R$ enedione 4.5 min, $t_R$ 7-hydroperoxides, 7-ols intermediates=6.8, 6.9, 7.0, 8.2 min. Later eluting impurities at 18 and 19 min are the 7-t-BuOO-cholesteryl acetates.

To the reaction mixture was added 550 mL MEK, 390 mL water, and 39 gms sodium sulfite. The mixture was heated to 70° C. until the enedione impurity was gone, about 3 hrs. The reaction mixture cooled, then was transferred to a separatory funnel and the aqueous layer cut and then the organic layer washed with 100 mL 1% brine. The MEK and t-BuOH were then removed by an azeotropic distillation with heptane (800 mL heptane added after an initial concentration to 300 mL) until less than 0.7% combined MEK and t-BuOH remained as assayed by GC (gas chromatography).

The heptane was checked for MEK and tBuOH levels by GC using an HP-5 column at 35° C. with a 0.5 mL flow rate. $t_R$ MEK=4.9 min, $t_R$ tBuOH=5.3 min, $t_R$ heptane=7.7 min. The volume was adjusted to 350 mL, cooled to −5° C. and filtered, washing twice with 150 mL 0° C. heptane. After drying, the product was obtained in 62% yield (51.5 gms total, 94 wt %, 97 A %) as an off-white solid. "A %" is area %.

Melting point (m.p.): 155–157° C.

NMR ($^1$H, 300 MHz, $CDCl_3$): 5.70 (s, 1H), 4.7 (m, 1H), 2.5–0.8 (m, 43 H), 0.6 (s, 3H).

Step 2:

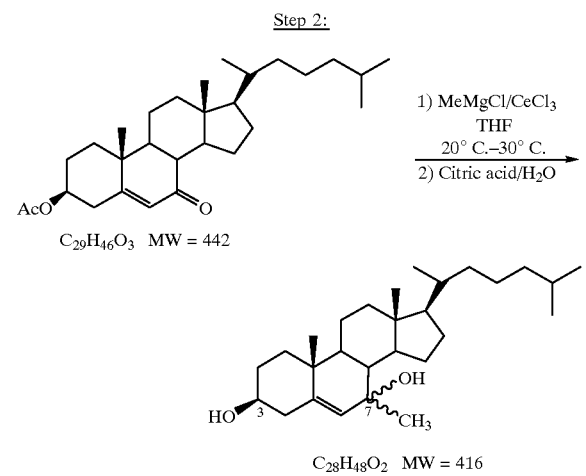

| Materials | Amt | | Mole | MW |
|---|---|---|---|---|
| 7-keto-cholesteryl acetate (95% pure) | 60 gm (as is) | | 0.13 | 442 |
| Methyl magnesium chloride (3.0 M) | 160 | mL | 0.48 | |
| $CeCl_3$ (anhydrous) | 16.6 | gm | 0.068 | 245 |
| THF (KF = 50 μg/mL) | 300 | mL | | |
| Citric acid | 115 | gm | 0.60 | 192 |
| water | 500 | mL | | |
| toluene | 600 | mL | | |
| sat'd $NaHCO_3$ | 240 | mL | | |

Anhydrous cerium chloride (16.6 gm) was stirred as a slurry in THF (150 mL) at 20° C. under $N_2$ for 2 h.

The cerium chloride was obtained as the hepta-hydrate and dried in vacuo at an oven temperature of 170° C. for three to four days. The dried cerium chloride showed a weight loss of 0.7% by T.G. analysis. After two hours a sample of the slurry was removed and showed fine needles under a microscope. To the slurry was added the Grignard reagent (160 mL) and the resulting light purple mixture was aged for 30 minutes.

To the cooled mixture (20° C.) was added the ketone (60 gm at 95% purity, 57 gm by assay) in THF (150 mL) over 50 minutes while allowing the mixture to exotherm to 30° C. Addition of the ketone to the Grignard reagent was exothermic, the exotherm was controlled by the rate of addition. The ketone solution in THF should be warmed to 30° C. to ensure complete dissolution, prior to adding it to the Grignard reagent.

The reaction progress was monitored by HPLC (high pressure liquid chromatography). A 0.5 mL sample was added to 10 mL of 0.1N HOAc and then diluted to 50 mL with $CH_3CN$. HPLC conditions [Zorbax® phenyl column, $CH_3CN$, water, phosphoric acid; 75:25:0.1 gradient elution to 90:10:0.1 at 18 minutes, flow=1.5 mL/min, UV detection at 200 nm]. Retention times, 3,7-diol $t_R$=5.6 and 5.9 min, starting ketone $t_R$=10.9 min, intermediate 7-OH, 3-OAc $t_R$=9.8 and 10.8 min. There was about 95 area % of 3,7 diol (ca. 85 mg/mL). (NOTE: Any remaining starting material or reaction intermediates can be converted into product using additional Grignard reagent.)

Once complete, the reaction was quenched by adding it to a 0° C. mixture of citric acid solution (115 gm in 300 mL of water) and toluene (360 mL). The quench was exothermic. (NOTE: The rate of addition should be carefully controlled to maintain an internal temperature below 10° C.)

The two phase mixture was stirred for 30 minutes and allowed to stand for 10–15 minutes for an adequate phase separation. The pH of the aqueous layer was ca. 2. The organic phase was separated, washed with water (200 mL, pH=3 after washing) and saturated NaHCO₃ solution (240 mL, pH=8 after washing). This afforded 750 mL of an organic layer which contained 66 mg/mL of diol for a yield of 49.5 gm (93%). The aqueous layer contained less than 1% of product.

The batch was concentrated to 300 mL in vacuo (100–200 mm), diluted to 600 mL with toluene and re-concentrated to 360 mL. The solvent switch to toluene was considered complete when the G.C. area % of THF was <2% of the toluene area %. (NOTE: The first 200 mL of the distillation has a tendency to foam at low pressures. Once this phase is complete, the vacuum should be brought down to 100 mm. The distillation temperature slowly rises from 20° C. to ca. 45° C. as the solvent switch to toluene nears completion.)

Samples of the distillate were assayed for residual THF using G.C. A sample of ca. 0.1 mL was diluted to 1 mL with methanol. G.C. conditions: [HP-5 column (25 M, 0.32 μm ID) using a heated block injector, 35° C. isothermal, flow= 0.5 mL/min], MeOH $t_R$=5.5 min, THF $t_R$=6.2 min, toluene $t_R$=10.1 min. The final assay was performed using a sample from the batch.

The organic layer contained 134.4 mg/mL of diols for a total yield of 48.4 gm (90%). (NOTE: The KF of the batch should be below 100 μg/mL before proceeding with the next step.)

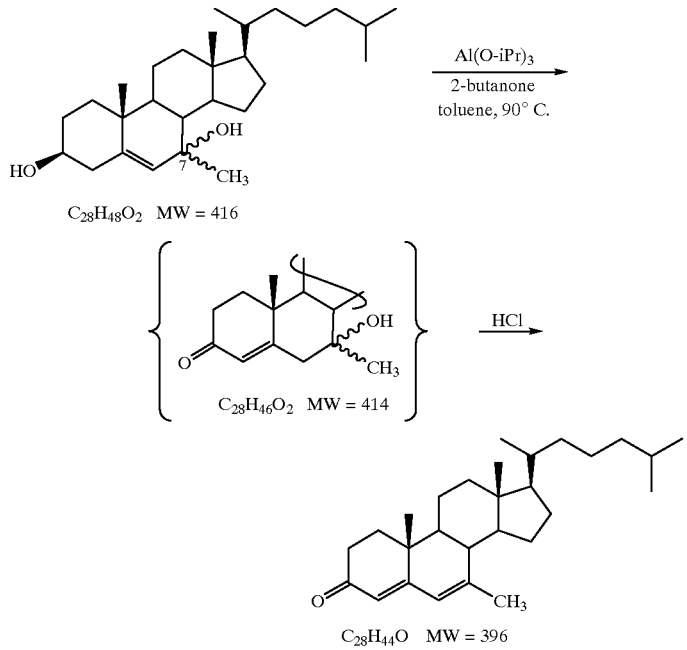

Step 3: OPPENAUER OXIDATION

| Materials | Amt | | MMole | MW |
|---|---|---|---|---|
| 7-methyl-7-hydroxy-cholesterol | 30.2 | g | 72.6 | 416 |
| 2-butanone (d = 0.805, KF = 480 μg/mL) | 126 | mL | 1404 | 72.11 |
| Aluminum isopropoxide | 18.9 | g | 93 | 204.25 |
| 3N HCl | 120 | mL | | |
| 5% NaCl solution | 120 | mL | | |
| Conc. HCl | 3.5 | mL | 42 | |
| D.I. water | 60 | mL | | |
| Saturated NaHCO₃ | 60 | mL | | |

To the toluene solution of the diol (256 mL, 118 mg/mL) was added 2-butanone (126 mL) and aluminum isopropoxide (18.9 g). The solution was heated to reflux (92° C.) under nitrogen. The reaction progress was monitored by HPLC.

The batch was assayed for 2-butanone content by G.C. prior to adding the aluminum isopropoxide. A sample of ca. 0.1 mL was diluted to 1 mL with MeOH. G.C. conditions [HP-5 column (25 m, 0.32 μm ID) using a heated block injector at 250° C., column temp at 35° C. isothermal, flow=0.5 mL/min] 2-butanone $t_R$=6.1 min, MeOH $t_R$=5.5 min, toluene $t_R$=10.1 min. The KF of the starting mixture was 70 μg/mL.

A 0.1 mL sample of the reaction mixture was quenched into 0.1N HOAc solution (2–3 mL) and then diluted to 10 mL with CH₃CN in a volumetric flask. HPLC conditions [25 cm Zorbax® Phenyl column; CH₃CN:H₂O with 0.1% phosphoric acid: 75:25 gradient elution to 90:10 at 18 min, hold 90:10 until 22 min; flow=1.5 mL/min, UV detection at 210 nm.] Starting diols $t_R$=5.4, 5.8 min, intermediate Δ-4 eneone $t_R$=6.4 min, dieneone $t_R$=12.1 min.

The reaction was considered complete when the level of starting diol was <3 area % (8 hours). Once complete the batch was cooled to 15–20° C. and quenched with 3N HCl (120 mL). The two phase mixture was stirred for 20 min, and then allowed to settle. The lower aqueous layer was removed and the organic layer was washed with 5% NaCl (120 mL). The batch was concentrated in vacuo to one half volume (40–60° C. at 150 mm). The distillation removed excess 2-butanone from the batch. The level of 2-butanone in the final batch was <2% of the toluene (using G.C.) and the KF was 60 μg/mL.

The toluene solution was treated with conc. HCl (3.5 mL) at 25° C., under $N_2$. The reaction was assayed by HPLC until the intermediate tertiary alcohol was completely converted to dieneone (ca. 1 h). The solution was washed with D.I. water (60 mL) and saturated $NaHCO_3$ (60 mL). The pH of the bicarbonate wash was 8.5. (NOTE: The decomposition reaction will turn black if run for longer than 8 hours.) The resulting red solution (128 mL) contained 202 mg/mL of dienone for a yield of 25.9 gm (90%).

Step 4: TRANSFER HYDROGENATION

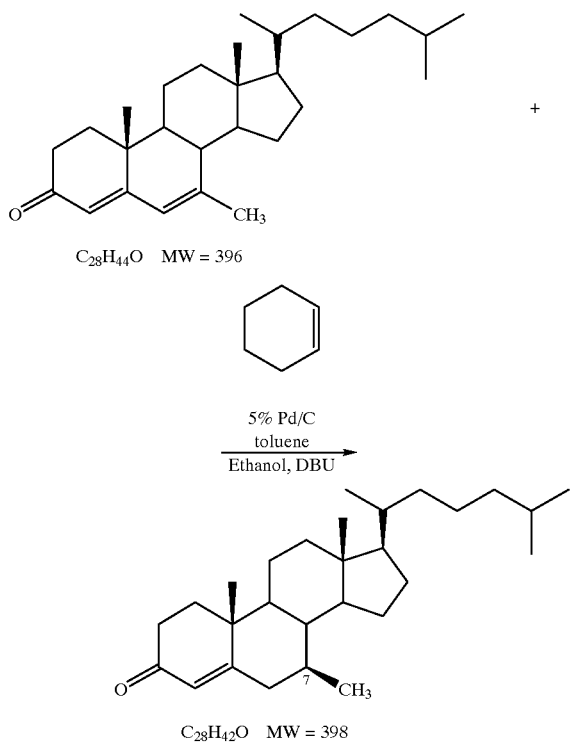

| Materials | Amt | | MMole | MW |
|---|---|---|---|---|
| Dieneone (toluene solution) | 31.5 | g | 79.5 | 396.7 |
| 5% Palladium on carbon (dry) | 4.5 | g | | |
| Cyclohexene (d = 0.811) | 120 | mL | 1.18 mole | 82.15 |
| 1,8 diazabicyclo[5.4.0]undec-7-ene (DBU) | 0.63 | mL | 4.2 | 152.2 |
| Absolute ethanol | 495 | mL | | |
| 3N HCl | 150 | mL | | |
| half saturated $NaHCO_3$ | 100 | mL | | |
| Solka Flok | | | | |
| Hexanes | 250 | mL | | |
| t-butanol | 175 | mL | | |

The toluene solution of the dieneone (150 mL at 214.6 mg/mL) was diluted with ethanol (120 mL) and cyclohexene (120 mL) and DBU (0.62 mL). To the mixture was added 5% palladium on carbon (9.0 g of 50% water wet). The mixture was degassed using vacuum/nitrogen purges (3×). The slurry was then heated to reflux (reflux temperature=72° C.). The reaction was monitored by HPLC.

A 2 mL sample of the reaction mixture was filtered through Solka Floe. The filtrate (0.1 mL) was diluted to 10 mL with $CH_3CN$ and analyzed by HPLC: 25 cm Zorbax® phenyl column; acetonitrile/water containing 0.1% phosphoric acid: gradient elution from 75:25 to 90:10 $CH_3CN$:water in 18 min, hold 90:10 until 22 min; flow=1.5 mL/min; UV detection at 200 nm.

Dienone $t_R$=12.1 min, Δ-4 enone $t_R$=13.2 min, Δ-5 enone $t_R$=14.1 min, over-reduced ketone $t_R$=14.4 min, ethyl enol ether $t_R$=20.9 min. The over-reduced ketone should be assayed at 192 nm.

The reaction was considered complete when the dieneone level was <2 A % and the Δ-5 enone level was 5% (about 10 hours). When the reaction was complete the mixture was cooled to ambient temperature. The palladium was removed by filtration through Solka Floc and the filter cake was washed with ethanol (150 mL).

The batch contained 51 mg/mL of enone. (NOTE: Prolonged reaction times should be avoided since over-reduction can occur. If the starting material has been consumed and the level of Δ-5 enone is >5% after 10 hours, then the palladium should be filtered, and the isomerization completed without catalyst present.)

The solution was concentrated under reduced pressure (75 mm) to a volume of approximately 150 mL. The batch was diluted with ethanol (225 mL) and re-concentrated to 150 mL.

The solvent switch to ethanol was considered complete when the toluene level was <2% of the ethanol by G.C., and there was no detectable cyclohexene. (NOTE: Removal of cyclohexene is important since it reacts in the subsequent oxidative cleavage step and unproductively consumes periodate.) A 0.1 mL sample was diluted to 1 mL with ethanol for the cyclohexene assay (and 1,1,1 trichloroethane for the toluene assay). G.C. conditions [HP-5 (25M×0.32 μm ID), using a heated block injector at 250° C., column temp at 35° C. isothermal, flow=0.5 mL/min] ethanol $t_R$=5.6 min, cyclohexene $t_R$=7.7 min, trichloroethane $t_R$=7.7 min, toluene $t_R$=10.2 min. The presence of cyclohexene is also detectable by $^1H$ NMR ($CDCl_3$) of the solution: cyclohexene vinyl protons at δ=5.64 ppm, eneone vinyl proton at δ=5.69 ppm.

The concentrate was diluted with hexanes (250 mL) and 3N HCl (150 mL). The two phase mixture was warmed to 40° C. until enol ether hydrolysis was complete. The layers were separated and the organic layer was washed with half saturated sodium bicarbonate (100 mL). The hexane phase had a volume of 291 mL, contained less than 5% ethanol by volume and assayed for 92 mg/mL of enone.

The solution was concentrated to 100 mL under reduced pressure (100 mm 15° C.). The batch was diluted with t-butanol (175 mL) and re-concentrated to 100 mL (100 mm/40° C.). The batch contained 260 mg/mL of the desired 7-β-methyl enone for a yield of 26.8 gm (85%).

(NOTE: These compounds could also be detected by G.C.M.S. Use of G.C. to follow this reaction should be avoided since the enone disproportionates on the column. G.C.M.S. conditions [HP-5 (25 M) column, on column injection at 285° C. isothermal]; over-reduced enone $t_R$=12.8 min, 7 alpha-epimer $t_R$=15.7 min, product $t_R$=17.3 min, s.m. $t_R$=21.3 min.

Step 5: OXIDATIVE CLEAVAGE

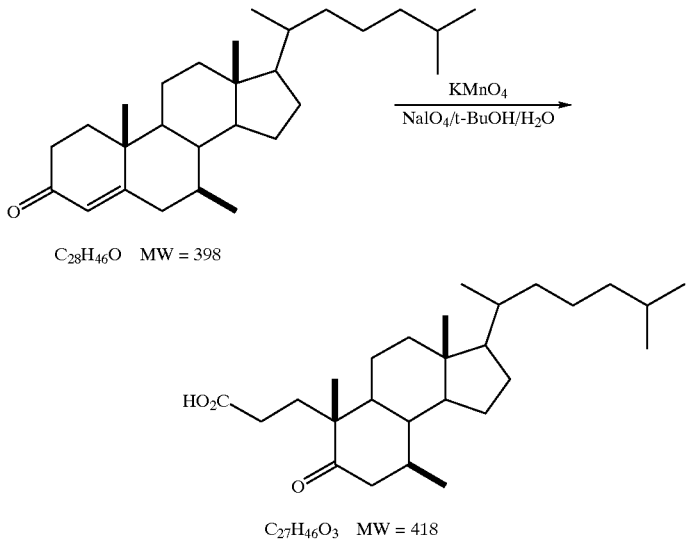

| Materials | Amt | Mol | MW |
|---|---|---|---|
| 7-β-Methylcholest-4-ene-3-one | 300 gm | 0.75 | 398 |
| t-Butanol (d = 0.786) | 6.6 L | | |
| Sodium carbonate | 159 gm | 1.5 | 106 |
| Sodium periodate | 1550 gm | 7.2 | 213.9 |
| Potassium permanganate | 11.1 gm | 0.07 | 158 |
| D.I. Water | 14.2 L | | |
| Diatomite | 50 gm | | |
| Ethyl acetate (d = 0.902) | 2.6 L | | |
| Heptane (d = 0.684) | 5.0 L | | |
| conc. Hydrochloric acid | 250 mL | | |
| 5% Aqueous NaCl | 2.5 L | | |
| Acetic acid (d = 1.049) | 9.0 L | | |

In a 5 L roundbottom flask was charged D.I. water (4.93 L), sodium periodate (1.55 Kg) and potassium permanganate (11.1 gm). The slurry was stirred at 65° C. for 30 minutes to obtain complete solution.

To a solution of the enone (300 gm) in t-butanol (4.60 L) was added a solution of sodium carbonate (159 gm) in water (2.3 L). The two phase mixture was warmed to 65° C. The enone should be toluene, ethanol and cyclohexene free. (NOTE: Concentration of enone in organic layer is about 56 mgmL$^{-1}$.) The sodium periodate solution was added to the enone solution over 3 h with rapid stirring, maintaining the reaction temperature at 65° C. The slurry was aged at 65° C. for 2 h. The periodate solution was added via a heated addition funnel.

Carbon dioxide gas was evolved during the reaction. A slow addition ensures controlled gas evolution. No exothermn was detected during addition. During the addition a purple/brown slurry was formed.

The reaction progress was monitored by HPLC. A 2 mL sample of the reaction mixture was cooled to 15° C. and filtered. The filtrate (0.1 mL) was diluted to 10 mL with water/CH$_3$CN (1:3). HPLC conditions [YMC Basic 25 cm×4.6 mm, CH$_3$CN, 0.01M H$_3$PO$_4$; 90:10 isocratic flow= 1.5 mL/min, UV detection at 200 nm]; enone $t_R$=11.5 min, seco-acid $t_R$=5.5 min.

The reaction was considered complete when the starting enone was <0.5 mg/mL. Water (3.0 L) was added and the slurry heated to reflux for 2 h to decompose any remaining KMnO$_4$ (color change from purple to brown) and to dissolve most of the solids precipitated on the vessel walls. The resultant slurry was cooled to 15° C. and filtered through dicalite (50 gm). The vessel and cake were washed with t-butanol/water (1:2, 6.0 L).

The filter cake was assayed for seco acid by dissolving 200–400 mg of cake with 50 mL water and 50 mL acetonitrile then filtering into the sample vial through diatomite to remove the small amount of orange manganese solids. The filtrates (pH=9.0–10.5) were extracted with heptane (5.0 L).

Ethyl acetate (2.6 L) was added to the aqueous mixture and the pH adjusted to 2.5±0.3 by the addition of conc. HCl (250 mL). The aqueous layer was removed.

The organic layer was washed with 5% aqueous brine (2×1.2 L). The ethyl acetate solution was concentrated (150 mm.Hg, 30° C.) to approx. 10% volume. Acetic acid (7.4 L) was added and the residual ethyl acetate removed by concentration (100 mm.Hg, 60° C.) to <1% by volume (<0.5 area % by HPLC). The final volume was adjusted to 5.0 L by addition of acetic acid. Ethyl acetate removal was monitored by HPLC using the conditions above except the flow rate was 0.5 mL min$^{-1}$ and UV detection at 210 nm. Ethyl acetate $t_R$=7.4 min, acetic acid $t_R$=6.9 min. The assay yield was 275 gm which represented an 88% yield. The acetic acid solution was used directly in the following step (ene-lactam formation).

Step 6: NH-Enelactam Formation

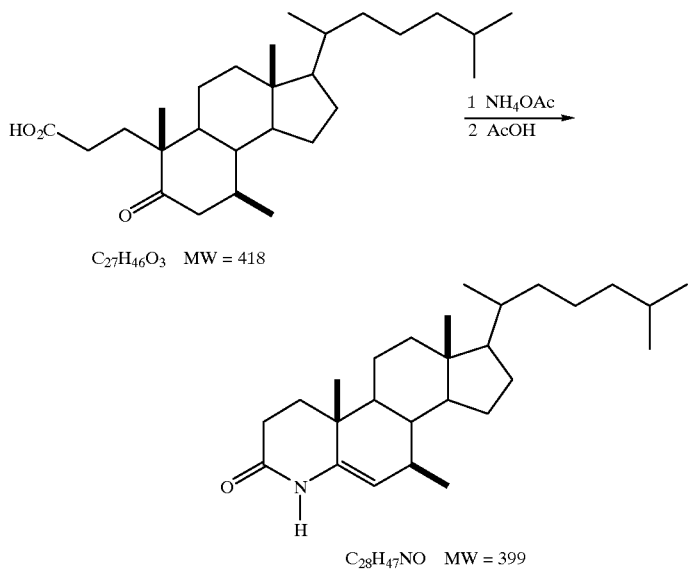

| Materials | Amt | Mole | MW |
|---|---|---|---|
| Seco-acid | 265 gm | 0.634 | 418 |
| Ammonium Acetate | 488 gm | 6.33 | 77.1 |
| 2,6-di-t-butyl-4-methylphenol (BHT) | 5.3 gm | 0.024 | 220 |
| D.I. Water | 565 mL | | |
| Acetic acid | 833 mL | | |

To a solution of seco-acid in acetic acid (265 gm in 5.3 L) obtained in the previous step was added BHT (5.3 gm) and ammonium acetate (488 gm) at 20° C. The slurry was warmed to a gentle reflux under a nitrogen atmosphere for 3 h. Complete solution was obtained at 30° C. The internal temperature was 120° C. at reflux. Color changed from yellow to dark red/brown. Use of reduced amounts of acetic acid results in oiling of the product at the crystallization stage.

The reaction progress was monitored by UPLC. HPLC conditions [SB Phenyl, $CH_3CN$, 0.01M $H_3PO_4$; isocratic 80:20 for 30 min, flow=1.5 mL/min, UV detection at 190/200 nm] Retention times: ene-lactam $t_R$=9.4 min, seco acid $t_R$=5.3 min. UV detection was at 190 nm for reaction progress and 200 nm for s.m. and product assay. The reaction was considered complete when <0.05 A % seco acid remained, about 3–4 hrs.

The reaction mixture was cooled to 60° C. and water (398 mL) added over 15 min. (NOTE: Addition of exactly 7.5% v/v water to the acetic acid solution is important.) The solution was allowed to cool to 50° C. and seeded with ene-lactam (1.0 gm). Crystallization occurred at 50° C. The slurry obtained was aged at 50° C. for 1 h and then cooled to 0–2° C. over 2 h.

The slurry was filtered and the light tan solid washed with 5:1 acetic acid/water (1.0 L). The solid was dried in vacuo at 30° C. overnight to give 255 gm at 87 wt % by assay (remainder is acetic acid) for an 88% yield. HPLC profile, UV at 200 nm was 99.4 A %. Melting point (m.p.) of solvate=112–115° C. Pure m.p.=175–178° C., softens at 162° C.

Step 7: NH-Enelactam Recrystallization

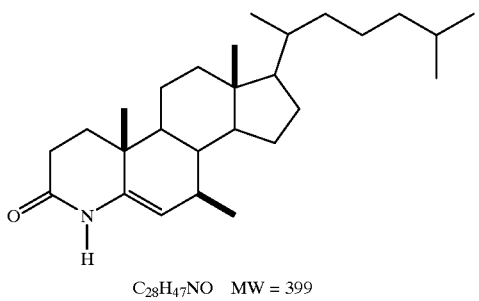

| Materials | Amt | Mole | MW |
|---|---|---|---|
| Enelactam | 20 gm | 0.041 | 400 |
| D.I. Water | 17 mL | | |
| Acetic acid | 133 mL | | |
| BHT | 0.20 gm | 0.00091 | 220 |

To 20 gm at 83 wt % enelactam was added 100 mL acetic acid which contained 200 mg of BHT. The slurry was warmed to 60° C. under a nitrogen atmosphere to achieve dissolution, then cooled to 50° C. A charge of 10 mL water was then added. The mixture was then cooled to 5° C. over 1.5 hrs, aged for one hour and then the solid filtered off. (NOTE: The solution at 50° C. should have started crystallizing before cooling to 5° C.) The solution KF after BHT addition was about 0.2–0.4% w/w.

The mother liquor amounts were monitored by HPLC. HPLC conditions [SB Phenyl, CH$_3$CN, 0.01M H$_3$PO$_4$, isocratic 80:20 for 30 min, flow=1.5 mL/min, UV detection at 200 nm] Retention times: ene-lactam $t_R$=9.4 min. Sample 100 μL and dilute to 10 mL with acetonitrile.

The slurry was filtered and the light tan solid washed with 5:1 acetic acid/water (40 mL) at 5° C. The solid was dried in vacuo at 30° C. overnight to give 18.5 gm at 84 wt % by assay (remainder is acetic acid) for a 94% recovery. HPLC profile, UV at 200 nm was 99.4 A %

M.p. solvate is 112–115° C. Pure m.p. is 175–178° C., softens at 162° C.

The reaction was monitored by HPLC, [25.0 cm Zorbax® phenyl SB, 90:10 CH$_3$CN: 0.01% H$_3$PO$_4$, 1.5 mL/min, Dual UV detection at 210 nm and 240 nm]. Retention times: enelactam 8.50 min, trans-lactam 12.4 min, cis-lactam 18.4 min. Sample 20 μL and dilute to 2 mL with acetonitrile.

On complete reaction (i.e., >99.9% conversion) the mixture was cooled to 20° C. and filtered through Solka-Flok (20 gm). The cake was washed with acetic acid (1.9 L). The filtrates were combined and concentrated at 30° C./10 mm.Hg to a volume of 570 mL. Heptane (total of 3.8 L) was added and concentration continued at atmospheric pressure (azeotrope b.p.=91–92° C.) to remove the acetic acid. (NOTE: Removal of the acetic acid to <0.2% by volume is

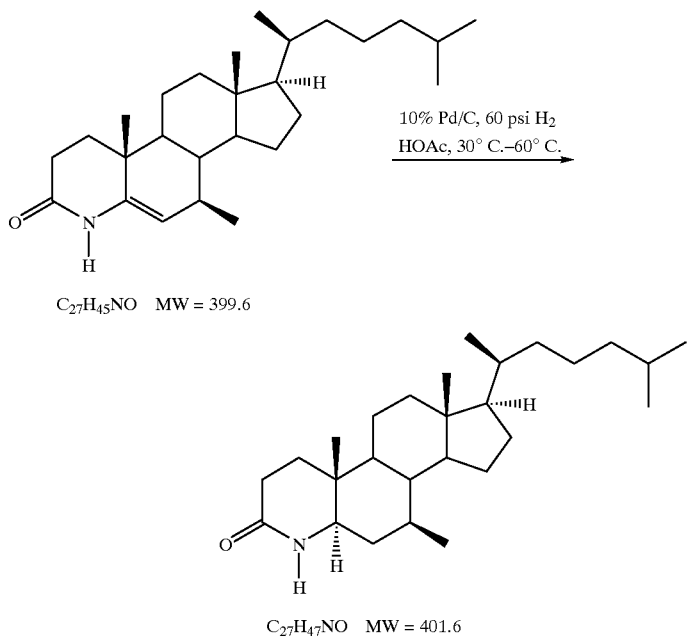

Step 8: N-H Enelactam Reduction

C$_{27}$H$_{45}$NO   MW = 399.6

C$_{27}$H$_{47}$NO   MW = 401.6

| Materials | Amount | Mol | MW |
|---|---|---|---|
| Enelactam (87 wt %) | 190.0 gm | 0.475 | 399.64 |
| HOAc (d = 1.05) | 3.8 L | | |
| BHT | 3.8 gm | 0.017 | 220.4 |
| 10% Pd/C (50% wet) | 38 gm | 10 wt % | |
| Hydrogen | 60 psi | | |
| Heptane | 3.8 L | | |
| MEK | 2.65 L | | |

BHT (3.8 gm) was dissolved in acetic acid (1.71 L) at 20° C. The solution was degassed with nitrogen purge for 30 min and the enelactam (218 gm at 87 wt %) added in one portion. The resultant solution was purged with nitrogen for 15 minutes. 10% Pd/C (50% wet) (38 gm) was added and the slurry transferred to a 1 gallon stirred autoclave. Degassed acetic acid (190 mL) was used to rinse the slurry into the autoclave. (NOTE: BHT must be added to the acetic acid prior to addition of the ene-lactam. The use of BHT stabilized acetic acid is necessary due to the oxidative instability of the ene-lactam.)

After vacuum purging with nitrogen the mixture was placed under 60 psi H$_2$ and stirred at 20° C. After 10 h at 20° C. the reaction temperature was increased to 60° C. until reaction was >99.9% complete.

important due to the very high solubility of the product in acetic acid.) Final b.p. was 98–99° C. Acetic acid was monitored at 200 nm by HPLC using a 25.0 cm Zorbax® phenyl SB column with 90:10 CH$_3$CN:water, 0.5 mL min$^{-1}$ as eluent. Sample 100 μL and dilute to 10 mL with acetonitrile.

The solution was concentrated to 570 mL and MEK (total of 2.5 L) added. The heptane was removed by azeotropic distillation at atmospheric pressure to <5% by volume as determined by G.C. of distillates and batch. G.C. Conditions: DB-5 20 m. 0.5 mL min$^{-1}$ Helium, 35° C. isothermal; MEK $t_R$=6.4, heptane $t_R$=8.0 min. Crystallization occurs during removal of heptane.

The volume was adjusted to 600 mL and the solution was allowed to cool to 20° C. over 3 h. The resultant slurry was aged at −10° C. for 2 h. The solid was collected on a filter frit and washed with cold MEK (150 mL). The solid was dried in vacuo at 20° C. Yield 170 gm, at >99 wt %; >99.2 A % at 210 nm. Step yield 89%.

The oil was kept under vacuum until the solvent level was <2%. The oil was poured into a glass tray and seeded with IV-a (1.25 gm) and allowed to stand in vacuo (20 mm.Hg) overnight.

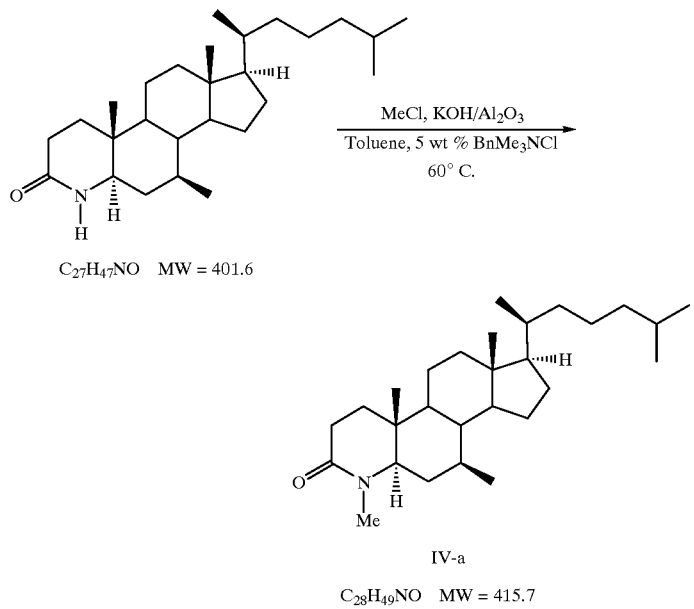

| Materials | Amount | Mol | MW |
|---|---|---|---|
| N-R Lactam | 3.0 Kg | 7.47 | 401.6 |
| Methyl chloride | 453 gm | 8.96 | 50.5 |
| KOH/Alumina[1:1] | 3.0 Kg | 22.8 | 56 |
| BnMe$_3$NCl | 150 gm | 0.81 | 185.7 |
| Toluene (d = 0.867) | 14.0 L | | |

A 5 gallon autoclave was charged with a slurry of lactam (3.0 Kg), BnMe$_3$NCl (150 gm) and potassium hydroxide on alumina (1:1, 3.0 Kg) in toluene (12 L) at room temperature. Methyl chloride (453 gm) was introduced at 20° C. with slow stirring. The slurry was heated to 65° C. with slow stirring and aged for 1 h. An exotherm at 52° C. of about 3° C. was noted as a spike on the temperature recorder.

The reaction progress was monitored by HPLC. HPLC conditions [Zorbax® SB phenyl, CH$_3$CN, 0.01M H$_3$PO$_4$; 90:10 isocratic, flow=1.5 mL/min, UV detection at 200 nm] lactam $t_R$=12.4 min, IV-a $t_R$=15.0 min. 25 µL Sample of toluene layer was diluted to 2 mL with acetonitrile. The reaction was monitored until complete conversion was obtained (>99.95%). The reaction was complete in <60 min at 60° C.

The reaction mixture was cooled to 20° C. and purged with nitrogen (4×) to remove any excess MeCl. The toluene solution was filtered through Solka Floc (100 gm) and the vessel and cake washed with toluene (2 L). The combined filtrates were concentrated at 100 mm. Hg and 20–30° C. to a residual oil. The oil should be homogeneous in heptane (10 mLg$^{-1}$) without any cloudiness.

The oil was assayed for toluene by G.C. oven temp 35° C. isothermal. The product (100 mg) was dissolved in methanol (0.5 mL) and 1 µL injected. Toluene $t_R$=4.4 min, methanol $t_R$=2.7 min.

The resulting solid was cut into blocks and broken up in a WARING blender containing 2° C. water (10 L) to a particle size of <50 µm. The slurry was filtered, washed with water (5.0 L) and dried in a nitrogen stream overnight. Yield of product=3.0 Kg, 97%.

EXAMPLE 2

Preparation of 7-keto cholesteryl acetate

The catalyst tris (triphenyl phosphine) ruthenium (II) chloride (96 mg, 0.1 mmol) was dissolved in chlorobenzene (10 mL), followed by cholesteryl acetate (4.3 gm, 10.0 mmol). The mixture was degassed with a vacuum nitrogen purge (3×), then cooled to +5° C. To the mixture under N$_2$ was added 90% t-butyl hydrogen peroxide (4.4 mL, 40 mmol) over 15 hours. HPLC assay showed 2.85 gm (65%) of the 7-keto cholesteryl acetate.

The batch was filtered through Solka-floc and the solvent was removed in vacuo. The residue was dissolved in methanol and then the batch was cooled to +5° C. and aged for 30 minutes. The batch was filtered and washed with cold methanol. The solid was air dried to afford 2.26 gm (51%) of 7-keto cholesteryl acetate.

Preparation of 7-keto cholesteryl acetate

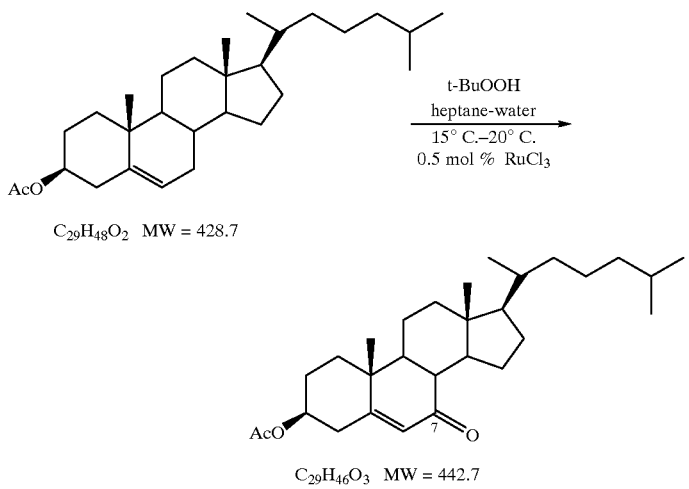

| Materials | Amt | Mole | MW |
|---|---|---|---|
| Cholesteryl acetate (95% Aldrich) | 78.1 gm | 0.173 | 428.7 |
| t-BuOOH (70 wt %, Aldrich) | 229 gm | 1.77 | 90.12 |
| RUCl$_3$-xH$_2$O | 0.24 gm | 0.00116 | 207.43 |
| Sodium sulfite (Na$_2$SO$_3$) | 39 gm | 0.309 | 126.04 |
| heptane | 310 mL | | |
| MEK (methyl ethyl ketone) | 550 mL | | |
| water | 445 mL | | |

In a 2000 mL 3-necked flask with an overhead stirrer was added ruthenium trichloride hydrate (240 mg), 55 mL water, cholesteryl acetate (78.1 gm) and heptane (310 mL). The stirring rate was 225–275 rpm with an overhead paddle stirrer.

70% t-BuOOH (229 gm) was added slowly over 4 hrs. An internal temperature of 15–20° C. was maintained by cooling with a water bath. The temperature of the batch began to rise slowly after an induction period of 5–15 min.

The reaction was stirred until less than 1.5 wt % of s.m. (starting material) and less than 2% of the 7-hydroxy cholesteryl acetate intermediate remained, about 20–24 hrs.

The reaction was monitored with a YMC basic column, 90:10 acetonitrile:water, flow rate=1.5 mL/min, UV detection at 200 nm. Retention times: $t_R$ cholesteryl acetate=17.0 min, $t_R$ 7-keto cholesteryl acetate=7.8 min, $t_R$ enedione 4.5 min, $t_R$ 7-hydroperoxides, 7-ols intermediates=6.8, 6.9, 7.0, 8.2 min. Later eluting impurities at 18 and 19 min are the 7-tBuOO-cholesteryl acetates.

To the reaction mixture was added 550 mL MEK, 390 mL water, and 39 gms sodium sulfite. The mixture was heated to 70° C. until the enedione impurity was gone, about 3 hrs. The reaction mixture was cooled then filtered through a pad of Solka-Flok to remove the ruthenium salts. The clear solution was transferred to a separatory funnel and the aqueous layer cut and then the organic layer washed with 100 mL 1% brine. The MEK and t-BuOH were then removed by an azeotropic distillation with heptane (800 mL heptane added after an initial concentration to 300 mL) until less than 0.7% combined MEK and t-BuOH remained as assayed by GC (gas chromatography).

The heptane was checked for MEK and t-BuOH levels by GC using an HP-5 column at 35° C. with a 0.5 mL flow rate. $t_R$ MEK=4.9 min, $t_R$ t-BuOH=5.3 min, $t_R$ heptane=7.7 min.

The volume was adjusted to 350 mL, cooled to −5° C. and filtered, washing twice with 150 mL 0° C. heptane. After drying, the product was obtained in 62% yield (51.5 gms total, 94 wt %, 97 A %), as an off-white solid.

EXAMPLE 4

Following essentially the same procedure as described in Example 1, Step 1, the compounds of Formula II were made from the corresponding starting materials of Formula I wherein Z is

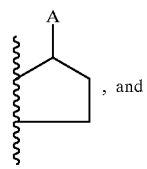, and

A, X and Y are defined as follows:
(a) A=6-methylhept-2-yl, X=—CH$_2$— and Y=—OH;
(b) A=ethylene ketal, X=—CH$_2$— and Y=ethylene ketal;
(c) A=t-butyl-di-methylsilyloxy (TBDMS-O—), X=—CH$_2$— and Y=—OC(O)CH$_3$; and
(d) A =6-methylhept-2-yl, X=—N(CH$_3$)— and Y=keto (=O)

Additionally, cyclohexenol was oxidized to cyclohexenone using essentially the same procedure as described in Example 1, Step 1.

The starting material for (b) was prepared by treating commercially available 4-androstene-3,17-dione with ethylene glycol and HCl using standard reaction conditions. The starting material for (c) was prepared by treating commercially available 5-androsten-3,17-diol-3-acetate with TBDMS-Cl and imidazole using standard reaction conditions. The starting material for (d) was prepared using standard synthetic procedures; i.e., oxidative cleavage of commercially available cholestanone (procedure described in Example 1, Step 5) followed by treatment with $NH_2CH_3$.

EXAMPLE 5

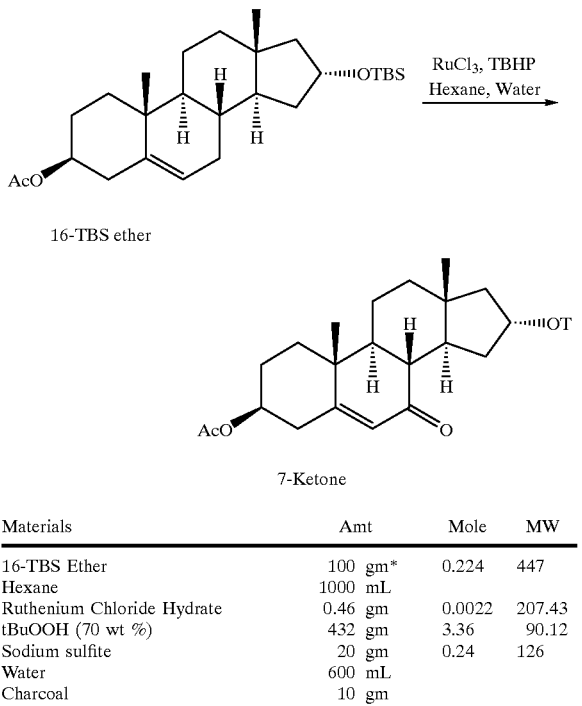

16-TBS ether

7-Ketone

| Materials | Amt | Mole | MW |
|---|---|---|---|
| 16-TBS Ether | 100 gm* | 0.224 | 447 |
| Hexane | 1000 mL | | |
| Ruthenium Chloride Hydrate | 0.46 gm | 0.0022 | 207.43 |
| tBuOOH (70 wt %) | 432 gm | 3.36 | 90.12 |
| Sodium sulfite | 20 gm | 0.24 | 126 |
| Water | 600 mL | | |
| Charcoal | 10 gm | | |

*Wt assay by HPLC

To a solution of the 16-TBS ether (100 gm by assay, 16-tert.-butylsilyl ether) in hexane (500 mL) at 20° C. was added water (300 mL) and ruthenium trichloride hydrate (0.46 gm). The two phase mixture was stirred and cooled to 10° C. tBuOOH (70 wt %) (432 gm) was added over 5 h while maintaining the reaction temperature 10–15° C.

The reaction is mildly exothermic. Water/ice was used to maintain the temperature between 10 and 15° C.

The reaction was followed by HPLC employing a ZOR-BAX Phenyl SB, 25.0 cm column, acetonitrile:water 30:70 to 80:20 over 25 min then held for 15 min. UV detection at 200 nm. 1.5 mLmin$^{-1}$.

| Retention times | Min |
|---|---|
| OTBS ether | 29.4 |
| 7-Ketone | 23.8 |
| TBHP | 3.25 |

The reaction is considered complete when <2% starting material remains (<1.5 mgmL-1).

Typical reaction time was 10 h.

After the reaction was completed, charcoal (10 gm) was added followed by sodium sulfite (20 gm) and the slurry stirred for 30 min.

The sodium sulfite decomposes any residual tBuOOH and other hydroperoxides. Addition of sodium sulfite was mildly exothermic and dependent on the residual tBuOOH concentration. Complete removal of tBuOOH was checked by HPLC. The two phase mixture was filtered through DICALITE (3" in sintered funnel) and the cake washed with hexane (300 mL). The aqueous layer was separated and the hexane layer washed with water (100 mL×2).

A small rag layer at the interface was removed by addition of acetonitrile (20 mL).

The hexane layer was concentrated to low volume and flushed with hexane (400 mL). The solution was concentrated to a final volume of 150 mL (approx. 2:1, hexane:substrate) and used 'as is' for the purification step.

The hexane solution was dried prior to silica treatment.

Silica Treatment

The hexane solution above was loaded onto a silica gel column (470 gm, 60–230 Mesh pre slurried in hexane). The column was eluted with hexane (800 mL) to remove unreacted starting material. The column was then eluted with 10% ethyl acetate in hexane (1000 mL) to provide the 7-ketone.

Column Details 100 mL fractions, column was followed by TLC (20% ethyl acetate/hex) or alternatively by HPLC (as above).

Fractions 14–17 were combined and concentrated to a total volume of 100.0 mL.

While the foregoing specification teaches the principles of the present invention, with examples provided for the purpose of illustration, it will be understood that the practice of the invention encompasses all of the usual variations, adaptations, and modifications, as come within the scope of the following claims and its equivalents.

What is claimed is:

1. A process for oxidizing a Δ-5-steroidal alkene to the corresponding Δ-5-7-keto-steroidal alkene comprising treating the Δ-5-steroidal alkene in solvent with a hydroperoxide in the presence of a ruthenium-based catalyst.

2. The process of claim 1 wherein the temperature of the reaction is from about −20° C. to about 100° C.

3. The process of claim 2 wherein the temperature is from about 5° C. to about 50° C.

4. The process of claim 3 wherein the temperature is about 15° C.

5. The process of claim 1 wherein the reaction is ran at an acidic pH.

6. The process of claim 5 wherein the pH is about 1.

7. The process of claim 1 wherein the reaction is run under an inert atmosphere.

8. The process of claim 1 wherein the solvent is selected from: water, toluene, ethyl acetate, hexane, chlorobenzene, 1,2-dichloroethane, heptane, t-butyl methyl ether, benzene, acetonitrile, cyclohexane, methylene chloride, t-butyl alcohol, and mixtures thereof.

9. The process of claim 1 wherein the ruthenium-based catalyst is a ruthenium sodium tungstate-based catalyst.

10. The process of claim 9 wherein the ruthenium sodium tungstate-based catalyst is $RuW_{11}O_{39}SiNa_5$.

11. The process of claim 1 wherein the ruthenium-based catalyst is selected from $RuW_{11}O_{39}SiNa_5$, $RuCl_3$, $RuCl_2(PPh_3)_3$, $Ru(acac)_3$, $Ru(dimethylglyoximato)_2(PPh_3)_2$, $RuO_2$, Ru/C, Ru(TPP)(CO)(THF), $Ru(bipy)_2Cl_2$, and $K_5SiRu(H_2O)W_{11}O_{39}$.

12. The process of claim 1 wherein the hydroperoxide is selected from t-butyl hydrogen peroxide, cumene hydroperoxide, hydrogen peroxide, and benzoyl peroxide.

13. The process of claim 12 wherein the hydroperoxide is t-butyl hydrogen peroxide.

14. The process of claim 13 wherein the ruthenium-based catalyst is RuW$_{11}$O$_{39}$SiNa$_5$.

15. The process of claim 14 wherein the solvent is heptane.

16. The process of claim 1 wherein the Δ-5-steroidal alkene and the Δ-5-7-keto-steroidal alkene have Formulas I and II, respectively:

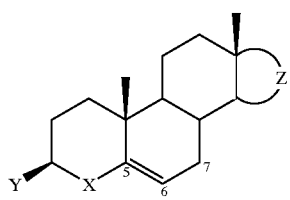

I

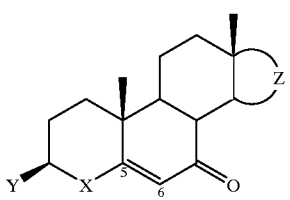

II wherein
Z is

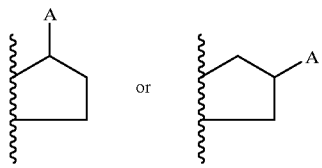

Y is selected from hydroxy, an esterified hydroxy group, keto and ethylene ketal; X is selected from —CH$_2$—, —NH— or —N(CH$_3$)— or —N-2,4-dimethoxybenzyl; and A is selected from:
—H, keto, protected hydroxy, acetate, hydroxy, protected amino, amino, C$_{1-10}$ alkyl, aryl-substituted C$_{1-10}$ alkyl, aryl carbamoyl-substituted C$_{1-10}$alkylC$_{1-10}$alkylcarbonyl, arylcarbonyl, ether-substituted C$_{1-10}$alkyl, keto-substituted C$_{1-10}$alkyl, heteroaryl-substituted C$_{1-10}$ alkyl, carboxylic ester, carboxamide, carbamate, substituted and unsubstituted anilide derivatives, urea, C$_{1-10}$ alkylcarbonylamino, ethylene ketal, ether and substituted and unsubstituted aryl ether.

17. The process of claim 16 wherein
(a) protected hydroxy is selected from dimethyl-t-butyl silyloxy, trimethylsilyloxy, tri-ethylsilyloxy, tri-i-propylsilyloxy, and triphenylsilyloxy;
(b) protected amino is acetylamino;
(c) C$_{1-10}$ alkyl is selected from methyl, ethyl, 1,5-dimethylhexyl, 6-methylhept-2-yl, and 1-methyl-4-isopropylhexyl;
(d) aryl substituted C$_{1-10}$ alkyl is selected from omega-phenylpropyl, and 1-(chlorophenoxy)ethyl;
(e) aryl carbamoyl substituted C$_{1-10}$ alkyl is 2-(4-pyridinyl-carbamoyl)ethyl;
(f) C$_{1-10}$alkylcarbonyl is isobutylcarbonyl;
(g) arylcarbonyl is phenylcarbonyl;
(h) ether-substituted C$_{1-10}$alkyl is selected from 1-methoxy-ethyl and 1-ethoxy-ethyl;
(i) keto-substituted C$_{1-10}$alkyl is 1-keto-ethyl;
(j) heteroaryl-substituted C$_{1-10}$ alkyl is omega-(4-pyridyl)-butyl;
(k) carboxylic esters are C$_{1-10}$ alkylcarboxylic esters selected from carbomethoxy and carboethoxy;
(l) carboxamides are selected from N,N-diisopropyl carboxamide, N-t-butyl carboxamide and N-(diphenylmethyl)-carboxamide;
(m) carbamates are selected from t-butylcarbamate and isopropylcarbamate;
(n) substituted or unsubstituted anilide derivatives are selected from wherein the phenyl may be substituted with 1 to 2 substitutents selected from ethyl, methyl, trifluoromethyl or halo (F, Cl, Br, I);
(o) urea is t-butylcarbonylamino urea;
(p) C$_{1-10}$ alkylcarbonylamino is t-butylcarbonylamino;
(q) ether is selected from n-butyloxy and ethylene ketal;
(r) substituted and unsubstituted aryl ether is selected from chlorophenyloxy, methylphenyloxy, phenyloxy, methylsulfonylphenyloxy and pyrimidinyloxy.

18. The process of claim 16 wherein Z is

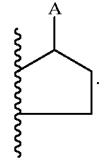

19. The process of claim 18 wherein A is selected from: 6-methylhept-2-yl, t-butylcarbamoyl, phenylcarbamoyl, 2,5-ditrifluoromethylphenylcarbamoyl, 4-methylsulfonyl-phenoxy, isobutylcarbonyl, phenylcarbonyl, 1-methoxyethyl, 1-keto-ethyl, 2-(4-pyridinylcarbamoyl) ethyl, and chlorophenoxyethyl.

20. The process of claim 18 wherein A is 6-methylhept-2-yl.

21. The process of claim 16 wherein Z is

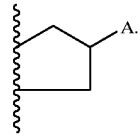

22. The process of claim 21 wherein A is: phenoxy, chlorophenoxy, methylphenoxy, 2-pyrimidinyloxy, and tert.-butylsilyloxy.

23. The process of claim 16 wherein the ruthenium-based catalyst is a ruthenium sodium tungstate-based catalyst.

24. The process of claim 23 wherein the ruthenium sodium tungstate-based catalyst is RuW$_{11}$O$_{39}$SiNa$_5$.

25. The process of claim 24 wherein Y is —OC(O)CH$_3$ and X is —CH$_2$—.

* * * * *